US00PP36386P2

(12) United States Plant Patent
Sheehan

(10) Patent No.: US PP36,386 P2
(45) Date of Patent: Jan. 14, 2025

(54) GRAPEVINE NAMED 'Sheegene 29'

(50) Latin Name: *Vitis vinifera*
Varietal Denomination: Sheegene 29

(71) Applicant: BLOOM FRESH INTERNATIONAL LIMITED, London (GB)

(72) Inventor: Timothy P. Sheehan, Vancouver, WA (US)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 18/606,554

(22) Filed: Mar. 15, 2024

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./156, 205, 206, 207
See application file for complete search history.

(56) References Cited

U.S. PATENT DOCUMENTS

PP4,787 P 11/1981 Olmo et al.
PP26,300 P3 * 1/2016 Lombard ..... A01H 5/08
Plt./205

* cited by examiner

*Primary Examiner* — Susan McCormick Ewoldt
(74) *Attorney, Agent, or Firm* — Michael Best & Friedrich LLP

(57) ABSTRACT

'Sheegene 29' is a new and distinct grapevine plant with novel characteristics that include good fertility, medium sized green (2.5 GY 6/2) seedless grape with a very good flavor for use in raisin production. The raisins have a unique candy-like apricot flavor and a bright golden color. The 'Sheegene 29' harvested period for fresh fruit is late August in the San Joaquin Valley of Central California.

1 Drawing Sheet

Latin name of the genus and species: *Vitis vinifera*.
Variety denomination: 'SHEEGENE 29'.

BACKGROUND

The present invention relates to a new and distinct variety of seedless grapevine named "Sheegene 29". 'Sheegene 29' produces medium-sized, green seedless grapes on bunches for use in raisin production. The new variety was first hybridized by Timothy P. Sheehan of Porterville, California as a cross of 'Flame' (not patented), as the pollen parent, and 'Red Globe' (U.S. Plant Pat. No. 4,787), as the seed parent, in 2000. The new variety was first asexually propagated in the dormant season of 2004, grafted on 'Harmony'(not patented), virus free rootstock, in a *Vitis vinifera* variety block located near Fowler, California. 'Sheegene 29' produces a golden seedless raisin (treated with sulfur and then dried in a dehydrator) that has a unique candy-like apricot flavor and a bright golden color that matures at the same time as 'Thompson Seedless'. All characteristics and distinctions remain true to form and are established and transmitted through succeeding propagations.

SUMMARY

The following are the most outstanding and distinguishing characteristics of 'Sheegene 29'. 'Sheegene 29' produces medium-sized green (2.5 GY 6/2) seedless grape with a very good flavor and matures for harvesting and shipping in late August in the San Joaquin Valley in Central California. The new variety most closely resembles 'Thompson Seedless' (not patented) but differs in fresh berry size and attachment strength. Specifically, 'Sheegene 29' fresh berry weight is 2.5 grams which is larger than the 2.0 grams berry weight for Thompson. The berries of 'Sheegene 29' have medium attachment strength and shatter is not an issue at full maturity as occurs with 'Thompson Seedless'.

The new variety is ideally suited for producing raisins by a dehydrator because its late maturity makes it not suitable for dried-on-vine raisin production. In the San Joaquin Valley, 'Sheegene 29' produces clusters of about 650 grams and the fruit reaches full maturity by late August with 20° Brix or more. Production potential is high and estimated at 60 Tn/hectare for fresh grape and 14-15 Tn/hectare for dry grapes, without impacting sugar maturity or production the following year. Raisin quality is excellent with good sensory qualities and similar appearance to 'Thompson Seedless' (not patented), 'Fiesta' (not patented) and 'Selma Pete' (not patented).

The new variety is distinguished from its male parent, 'Flame' (not patented) in that 'Sheegene 29' produces green-colored grapes while 'Flame' produces red colored grapes. 'Sheegene 29' matures two weeks later than 'Flame'.

'Sheegene 29' is distinguished from its female parent, 'Red Globe' (U.S. Plant Pat. No. 4,787), in that the new variety produces green seedless grapes, as compared to its seed parent 'Red Globe' (U.S. Plant Pat. No. 4,787), that produces seeded grapes. The vigor of 'Sheegene 29' is greater than 'Red Globe'.

'Sheegene 29' presents characteristics that distinguish it from other raisin cultivars, such as large leaves that are deeply lobed and overlapped, lateral shoots that are infrequent, and lateral clusters that are absent. Lateral clusters are also absent on Sheegene 28 (U.S. Plant Pat. No. 34,211). Vigor is medium-high which is similar to 'Thompson Seedless', 'Selma Pete', 'Sheegene 27', (U.S. Plant Pat. No.

29,129) 'Sheegene 28', and 'Flame Seedless'. Vigor is greater than 'Fiesta'. Sugar maturity is similar to 'Thompson Seedless', a week later than 'Selma Pete' and 'Sheegene 27', and three to four weeks later than 'Sheegene 28'.

BRIEF DESCRIPTION OF THE DRAWINGS OR PHOTOGRAPHS

The accompanying colored photographs illustrate the overall appearance of the 'Sheegene 29' plant showing the colors as true as it is reasonably possible to obtain in colored reproductions of this type. Colors in the photographs may differ slightly from the color values cited in the detailed botanical description that accurately describe the colors of the plant described herein. These figures are exemplary and will vary depending on the plant and distinguishing characteristics.

FIG. 1 shows the form, foliage, and fruit of a 5-year-old 'Sheegene 29' vine grown in a field in California, USA. The colors shown are as true as can be reasonably obtained by conventional photographic procedures.

DETAILED BOTANICAL DESCRIPTION

The following detailed description sets forth the distinctive characteristics of 'Sheegene 29'. The detailed botanical description was obtained between March and November using 4-year-old plants grown in fields in California, USA. The color references are to the Munsell Plant Tissue Color Book, 2012 Edition by Munsell Color.

Classification:

*Family*.—Vitaceae.

*Botanical*.—*Vitis vinifera*.

*Common name*.—Grapevine.

*Cultivar name*.—'SHEEGENE 29'.

Plant:

*Plant habit and growth*.—Semi-erect; primary shoots bear at least two clusters; moderate number of lateral shoots. Lateral shoots do not bear clusters (secondary bunches).

*Age at maturity*.—5 years old.

*Size* (*at maturity*).—Height: 238 cm. Width: 190 cm.

*Vigor*.—Medium-high.

*Productivity*.—High (1.1 fertility index), around 24 Tn/acre (60 Tn/hectare).

*Rootstock*.—Name of rootstock: Freedom (not patented). Age of rootstock at time of grafting: one year old.

Trunk:

*Size*.—Diameter: 6.4 cm. Height (at measured diameter of 6.4 cm): 30 cm above the ground.

*Shape*.—Round trunk.

*Surface texture*.—Rough texture, striated.

*Bark color*.—Exterior: 2.5 YR 5/4. Interior: 5 YR 3/4.

Canes:

*Size*.—Diameter: 14.7 mm measured at 5th node around harvest time (mature vine). Length: 256 cm in average.

*Surface texture*.—Mature cane: finely ribbed to smooth. Immature cane: smooth.

*Form* (*woody shoot cross section form*).—Pith in center with diaphragm at nodes.

*Color*.—Mature: 5 months, 7.5 GY 4/4. Immature: 4 weeks, 7.5 GY 6/6. Dorsal side of internodes: 7.5 GY 6/6. Ventral side of internodes: 2.5 GY 5/8. Dorsal side of nodes: 2.5 GY 6/8. Ventral side of nodes: 2.5 GY 6/8.

*Internode length* (*upper mature sun cane*).—6 cm in average.

*Internode width* (*upper mature sun cane*).—1.23 cm in average.

*Node width*.—2.18 cm in average.

Bud:

*Bud description*.—Winter bud: pointed, color 7.5 TR 8/2. Green bud: pointed, 2.5 GY 6/8.

*Time of bud burst*.—50% bud burst at Mar. 25, 2023.

*Time of bud leaf burst*.—50% bud break at Mar. 30, 2023.

Tendrils:

*Form*.—Mostly bifid, rarely trifid.

*Size*.—Length: 15.16 cm in average. Diameter: 2 mm in average.

*Texture and distribution of tendril at each node beginning at base*.—Smooth, discontinuous, 00000010101101 (0 means no tendril at that node and 1 means there is tendril at the node).

*Color*.—Mature: 4 weeks, 2.5 GY 5/8. Immature: 10 days, 2.5 GY 5/8.

*Anthocyanin*.—Mature: not present. Immature: 5 Y 5/6.

Growing tips (young shoot):

*Pubescence*.—White pubescence, and slightly wooly.

*Color*.—2.5 GY 7/6.

*Anthocyanin*.—Absent.

*Shape*.—Half-open.

*Apex*.—Triangular.

*Form of tip*.—Curved.

*Shoot attitude before tying*.—Semi-erect.

Leaves:

*Shape*.—Cuneiform, overlapped lobes, punch holes, deeply lobed, long apical lobe, some teeth on sinus, wavy leaf.

*Apex*.—Slightly pointed.

*Base*.—Overlapped lobes and closed petiolar sinus.

*Number of lobes*.—5.

*Depth of upper lateral sinuses of mature leaves*.—Deeply lobed.

*Arrangement of lobes of upper lateral sinuses on mature leaves*.—Overlapped lobes.

*Margin*.—Rounded slightly pointed teeth.

*Length of teeth on margin*.—7.4 mm in average.

*Shape of teeth on margin*.—Short teeth two convex sides.

*Texture* (*mature leaf*).—Upper surface: rugose, bumpy and blistered surface. Lower surface: rough surface.

*Size*.—Immature: Length: 10 days, 6.55 cm (fourth leaf from shoot tip). Width: 10 days, 7.65 cm. Mature: Length: 4 weeks, 13.85 cm (leaves around the fruit zone). Width: 4 weeks, 15.35 cm.

*Ratio of length/width of teeth* (*mature leaf*).—Small.

*Color*.—Immature leaf: Upper surface: 5 GY 4/8. Lower surface: 5 GY 5/4. Mature leaf: Upper surface: 7.5 GY 3/4. Lower surface: 7.5 GY 5/4. Autumn coloration: Upper surface: 2.5 Y 7/4. Lower surface: 2.5 Y 8/4.

*Venation*.—Pattern: palmate (veins on upper leaf are flat; veins on lower leaf are raised). Length of middle vein in mature leaves: 15 cm in average. Color: Upper surface: 2.5 GY 7/4. Lower surface: 2.5 GY 7/6.

*Petiolar sinus*.—Closed to slightly open.

*Petiole*.—Length: 11.2 cm. Diameter: 2.83 mm. Color: Dorsal: generally green (2.5 GY 7/9) with some red (10 R 5/6). Ventral: 2.5 GY 7/4.

Floral cluster:

*General description and location*.—Mostly in the 4th and 5th node. Most cluster have a conical shouldered shape, with 80% of them having a long wing.

*Quantity of inflorescences per cluster*.—Around 2000 inflorescences per cluster.

*Size*.—Length: 21.23 cm. Width: 18.13 cm.

*Peduncle*.—Length: 5.6 cm.

*Inflorescences*.—Hermaphroditic.

*Stamens*.—5 per flower, upright, straight, 3.12 mm.

*Anthers*.—Are divided, yellow white.

*Date of bloom*.—Start: 13 May, 50%: 15 May, 100%: 19 May.

*Pollen amount*.—Moderate.

*Calyptra*.—5 segments and complete detachment.

*Calyptra color*.—5 GY 5/6.

Fruit:

*Time of year of commercial harvest and shipment*.—August 15th-September 30th, in California, USA.

*Time of beginning of berry ripening*.—Medium to late season.

*Keeping quality*.—Dried fruit can be stored for up to 3 years.

*Cluster* (*primary bunches*).—General size: medium to large (650 g in average). Length (without peduncle): 24.5 cm in average. Width: 17.3 cm hanging, 25.5 cm with shoulders spread. Density: medium. Peduncle length: 4.2 cm. Peduncle diameter: 6.2 mm. Peduncle color: 5 GY 7/14, lignified section is 7.5 YR 5/6. Number of berries per cluster: 260 (on average). Berry: Size: medium (2.5 g/berry). Diameter: 16.8 mm. Length: 19.34 mm. Shape: short ellipsoidal to ovoid. Uniformity: sightly not uniform. Brix content: 20° Brix on August 31st. Titratable acidity: 0.47% on August 31st. Skin color (without bloom): 2.5 GY 6/6. Skin color (with bloom): 2.5 GY 6/2. Pedicel: Length: 7.04 mm. Diameter: 1.35 mm. Color: 2.5 GY 5/8. Strength of attachment to berry: medium.

*Cluster* (*secondary bunches*).—No secondary cluster found.

Berry flesh:

*Color*.—2.5 GY 8/4.

*Juice, color*.—Clear.

*Juice production*.—Medium.

*Thickness of skin*.—Thin.

*Flavor*.—Sweet neutral.

*Fragrance*.—No fragrance.

*Texture*.—Soft.

*Seeds*.—No.

*Use*.—Raisins.

Dry product:

*Dried berries* (*raisins*).—Average moisture content — Around 11.1%.

*Raisin length*.—1.4 cm.

*Raisin width*.—1.2 cm.

*Raisin weight*.—Around 0.625 g.

*Raisin color*.—Ranges from 7.5 YR 5/8 to 2.5 Y 8/8.

*Raisin flavor*.—Distinct apricot flavor, balanced acidity.

*Dry cluster length*.—19.6 cm.

*Dry cluster width*.—14.3 cm.

*Dry cluster weight*.—Around 160 g.

*Raisin yield*.—Approximately 10 to 14 Tn/ha, assuming a vine density of 1,543 vines per hectare.

*Keeping quality*.—Excellent, dried fruit can be stored for up to 3 years, sustained apricot flavor, sugar crystals are not an issue. Golden color tends to fade with time.

*Raisin quality*.—Approximately 82.7% B or better grade.

Disease and insect resistance: This cultivar is susceptible to diseases of its species, such as *Erysiphe necator, Plasmopara viticola, Botrytis cinerea, Daktulosphaira vitifoliae, Ceratitis capitata, Planococcus ficus, Planococcus citri*, and *Empoasca vitis*.

What is claimed is:

1. A new and distinct variety of *Vitis vinifera* named 'Sheegene 29' as described and illustrated.

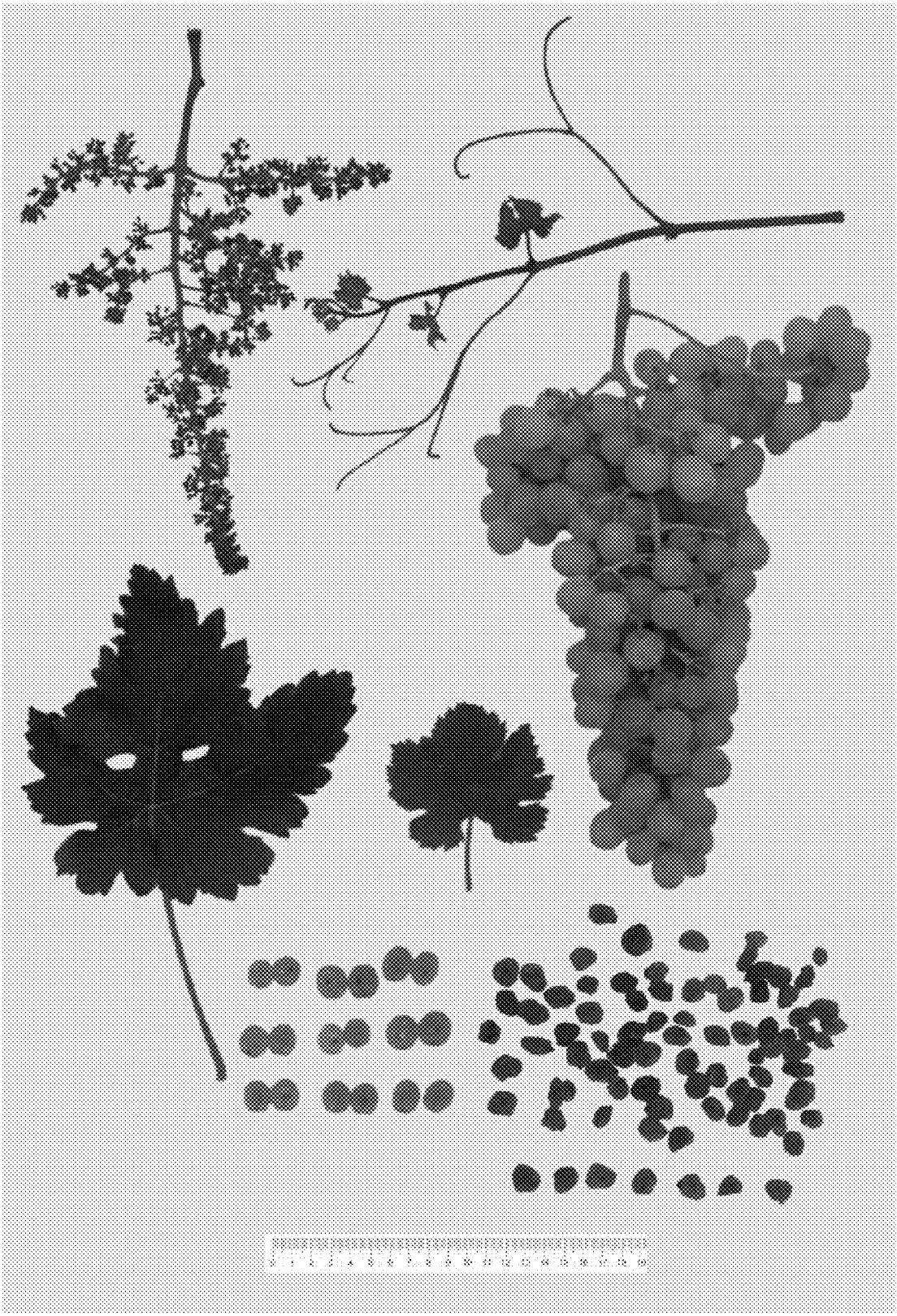

* * * * *